United States Patent
Lin et al.

(10) Patent No.: US 8,683,669 B2
(45) Date of Patent: Apr. 1, 2014

(54) BONE PLATE MANUFACTURING METHOD

(75) Inventors: Ting-Sheng Lin, Kaohsiung (TW); Chih-Yu Chen, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 427 days.

(21) Appl. No.: 13/106,931

(22) Filed: May 13, 2011

(65) Prior Publication Data
US 2012/0285002 A1   Nov. 15, 2012

(51) Int. Cl.
*B23Q 17/00*   (2006.01)

(52) U.S. Cl.
USPC ..................................................... 29/407.01

(58) Field of Classification Search
USPC ........... 29/592, 407.01, 407.04, 527.2, 527.1; 606/282, 280, 298; 345/419; 128/898; 600/407; 264/138
See application file for complete search history.

(56) References Cited

U.S. PATENT DOCUMENTS

| | | | |
|---|---|---|---|
| 4,436,684 A * | 3/1984 | White | 264/138 |
| 5,373,860 A * | 12/1994 | Catone | 128/898 |
| 5,741,215 A * | 4/1998 | D'Urso | 600/407 |
| 7,603,192 B2 | 10/2009 | Martin et al. | |
| 7,618,419 B2 | 11/2009 | Lavallee | |
| 7,740,634 B2 | 6/2010 | Orbay et al. | |
| 2010/0228252 A1 | 9/2010 | Courtney et al. | |

* cited by examiner

*Primary Examiner* — John C Hong
(74) *Attorney, Agent, or Firm* — Alan Kamrath; Kamrath IP Lawfirm, P.A.

(57) ABSTRACT

A bone plate manufacturing method includes an image acquisition step, an image reconstruction step, a comparison step, a data retrieval step, a model designing step and a bone plate manufacturing step. The image acquisition step acquires an original 3D craniofacial image. The image reconstruction step uses an image processing system to perform image reconstruction of the original 3D craniofacial image to obtain a reconstructed 3D craniofacial image, and the image processing system comprises a plurality of mechanical data. The comparison step compares the original 3D craniofacial image with the reconstructed 3D craniofacial image and defines the image difference therebetween as a defected portion. The data retrieval step retrieves a portion of the mechanical data and defines a mechanical compensation area on the reconstructed 3D craniofacial image. The model designing step designs a bone plate mold. The bone plate manufacturing step manufactures a bone plate.

6 Claims, 6 Drawing Sheets

BONE PLATE MANUFACTURING METHOD

BACKGROUND OF THE INVENTION

1. Field of the Invention

The present invention generally relates to a bone plate manufacturing method and, more particularly, to a bone plate manufacturing method adopted to craniofacial surgeries.

2. Description of the Related Art

Craniofacial surgery has been an important surgery among surgical operations and is directed to congenitally oral and maxillofacial malformation, acquired injuries (such as fracture), or facial defects caused by tumor excision. Generally, surgeons rely on a 2D (two-dimensional) computerized axial tomography (CT) scan or a computer-established 3D (three-dimensional) craniofacial model to proceed preoperative tasks prior to craniofacial surgery. Then, the surgeons will determine which location and angle a bone plate should be implanted into the cranioface of a patient based on their domain experiences, to reconstruct the fragmentary or deformed cranioface.

Because a conventional bone plate is usually manufactured in an injection molding manner, the produced bone plate is of predetermined shape and size.

In general, surgeons often bend the conventional bone plate (which has predetermined shape and size) in a proper angle and direction by hands into a desired shape that fits to the area and shape of an injury part of the cranioface of the patient. Thus, the bent bone plate can be positioned on a proper location of the cranioface of the patient, allowing the broken bones of the cranioface of the patient to be fixed or repaired via the bent bone plate.

Since the structure, shape, spatiality and thicknesses of human cranioface are in a great complexity, as well as since the cranioface includes the supramaxilla and submaxillary that involve occlusion, eating, gums arrangement and facial looks, the conventional bone plate with inflexible shape and size can not properly fit to the injury part of the cranioface of the patient. This results in inconvenience in using the conventional bone plate. Moreover, since the conventional bone plate is manually bent by hands, the bent bone plate may not fully fit to the area and shape of the injury part of the cranioface of the patient, resulting in difficulty in accurately positioning the bent bone plate on the cranioface of the patient. As a result, the performance of craniofacial reconstruction is greatly affected.

Due to the problems stated above, the craniofacial surgery employing the conventional bone plate may require a longer healing time for patients. In a worse case, the patient who underwent the craniofacial surgery may have problems in occluding and chewing properly, or even have a disordered gums arrangement that leads to poor healing of the injured part. This affects the facial appearance of the patient negatively and makes the facial actions of the patient awkward. It takes a long time and several labionasal plastic surgeries for most patients to regain lip and palate functions.

U.S. Pat. No. 7,603,192 discloses another bone plate manufacturing method that establishes one or more 3D graphical models using a CT scan and physical model. The method generates X, Y and Z planes for each 3D graphical model so that complete 3D graphical models of an affected part and a bone plate can be obtained. The method finally compares the 3D graphical models and accordingly creates a design of the bone plate that can be well-fitted to the affected part of the patient.

However, the above bone plate manufacturing method merely improves the fitting between the bone plate and the bone surface of the affected part without taking some important factors into consideration, such as the mechanical factor associated with the forces acted upon the bone plate and the affected part, the craniofacial appearance and occlusion function etc. Therefore, the bone plate manufactured by the above bone plate manufacturing method can only be applied to limb bones which have a regular shape and relatively even thickness (compared to human cranioface) and do not suffer complex forces.

Since a human cranioface has a much more complex structure and can suffer multiple forces, the craniofacial bones tend to have compound fractures. Thus, the bone plate manufactured by the above conventional bone plate manufacturing method, which does not take the mechanical factor between the bone plate and the affected part into consideration, is not applicable to craniofacial reconstruction. This is because the bone plate is not able to provide sufficient accuracy in craniofacial reconstruction in such a complex craniofacial structure while the facial appearance and the functions of the supramaxilla and submaxillary are still maintained.

SUMMARY OF THE INVENTION

It is therefore the primary objective of this invention to provide a bone plate manufacturing method that designs a bone plate, which is to be fitted to an affected part of a patient's cranioface, based on mechanical conditions of the affected part, thus improving the accuracy of craniofacial surgeries.

It is another objective of this invention to provide a bone plate manufacturing method that shortens the required healing time after operations.

The invention discloses a bone plate manufacturing method comprising an image acquisition step, an image reconstruction step, a comparison step, a data retrieval step, a model designing step and a bone plate manufacturing step. The image acquisition step acquires an original 3D craniofacial image of a patient. The image reconstruction step uses an image processing system to perform an image reconstruction of the original 3D craniofacial image to obtain a reconstructed 3D craniofacial image, and the image processing system comprises a plurality of mechanical data specifying mechanical parameters of various parts of a cranioface. The comparison step compares the original 3D craniofacial image with the reconstructed 3D craniofacial image via the image processing system, and defines the image difference therebetween as a defected portion. The data retrieval step retrieves a portion of the plurality of mechanical data that corresponds to the defected portion, and defines a mechanical compensation area on the reconstructed 3D craniofacial image that compensates the portion of the plurality of mechanical data of the defected portion. The model designing step designs a bone plate mold with a thickness based on the surface shape of the mechanical compensation area. The bone plate manufacturing step manufactures a bone plate using the bone plate mold.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the terms "first", "second", "third", "fourth", "inner", "outer," "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

It is firstly defined that the term "mechanical data" mentioned hereinafter refers to mechanical information that specifies the strength and directivity of a force acted upon a certain part of the human cranioface during a certain action of the human cranioface. For example, when the submaxillary performs occlusion, the mechanical data specifies the strength and directivity of a force (which is caused by the occlusion) acted upon the submaxillary.

The invention discloses a bone plate manufacturing method executed by an image processing system according to a preferred embodiment of the invention. The image processing system comprises at least a central processing unit (CPU) and at least a database connected to the CPU. The database pre-stores a plurality of mechanical data specifying mechanical parameters of various parts of a human cranioface (such as the strength and directivity of forces acted upon various parts of the human cranioface). For example, when the submaxillary performs occlusion, each of the plurality of mechanical data specifies mechanical information such as the strength and directivity of the force acted upon an individual point of the submaxillary. Each mechanical data further specifies mechanical information regarding average bearing stress, functionality, range of acting force, the part where force is exerted, and the mechanical requirement of various parts of a human cranioface of predetermined sampling groups (such as different race, age, gender, etc). In a preferred case, the database further stores extra mechanical information that can benefit bone plate manufacturing, such as general bone spatiality, bone structure, bone thickness and bone combinations of the human cranioface of the predetermined sampling groups.

The bone plate manufacturing method of the invention can produce a tailor-made craniofacial bone plate designed with mechanical consideration for those patients with congenital or acquired craniofacial defects.

Figure 1:
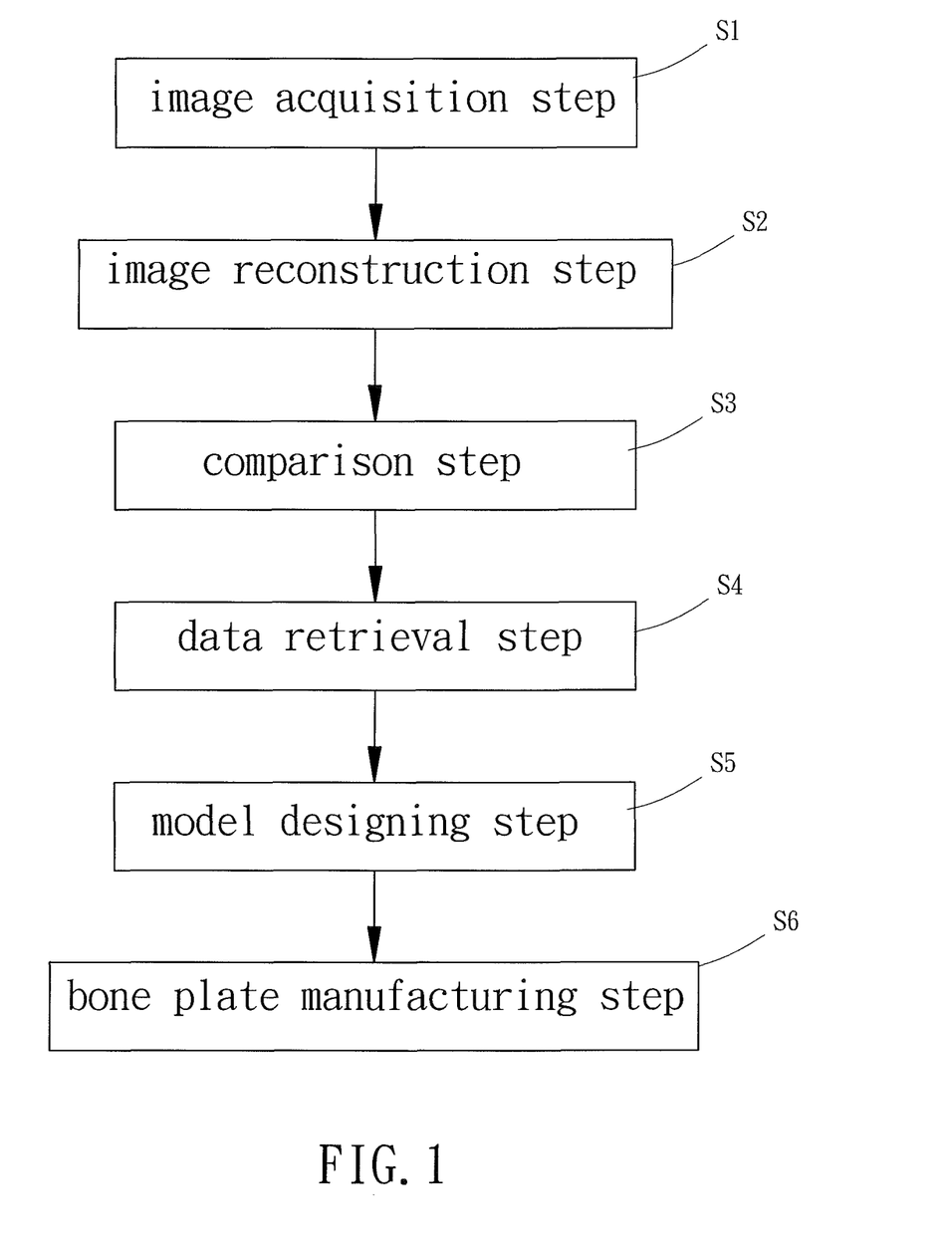
FIG. 1 shows a flowchart of a bone plate manufacturing method according to a preferred embodiment of the invention.

Referring to FIG. 1, the bone plate manufacturing method of the invention comprises an image acquisition step S1, an image reconstruction step S2, a comparison step S3, a data retrieval step S4, a model designing step S5 and a bone plate manufacturing step S6.

Figure 2:
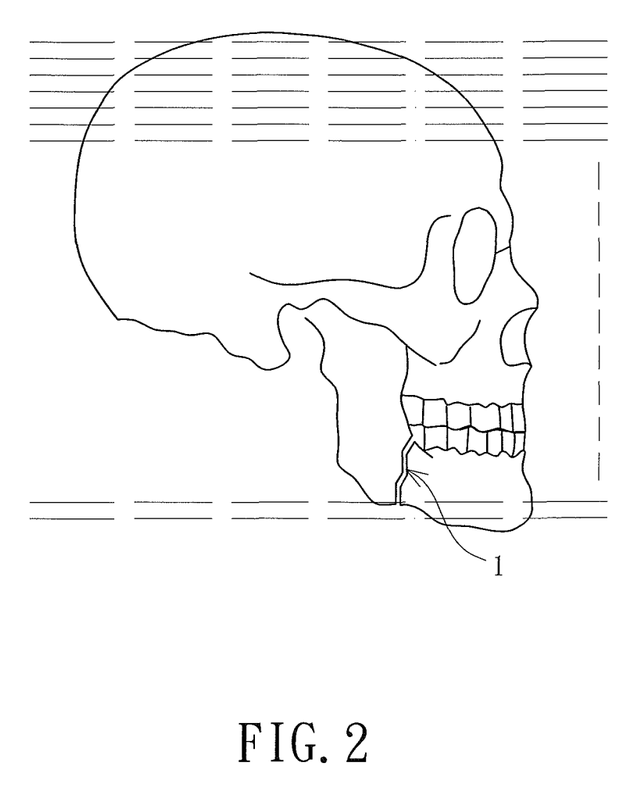
FIG. 2 shows an operation diagram of an image acquisition step of the bone plate manufacturing method of the invention.
Figure 3:
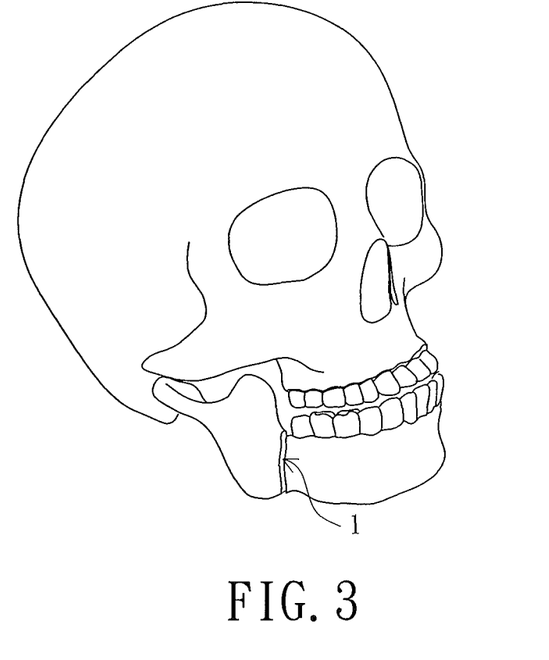
FIG. 3 shows another operation diagram of the image acquisition step of the bone plate manufacturing method of the invention.

Referring to FIGS. 2 and 3, the image acquisition step S1 is provided to acquire an original 3D craniofacial image of a patient. For example, the image acquisition step S1 may acquire CT or MRI (Magnetic Resonance Imaging) images of the patient with craniofacial defects through a medical instrument that can perform scanning of the cranioface of the patient. Then, methods such as Ray-casting, Cuberille, Marching Cubes, Dividing Cubes, Extended Ray-casting or Extended Cuberille are employed to perform a surface reconstruction for the acquired images to obtain the original 3D craniofacial image of the patient. The original 3D craniofacial image includes the injured part (or defected part) 1 of the cranioface of the patient, as shown in FIG. 3.

Figure 4:
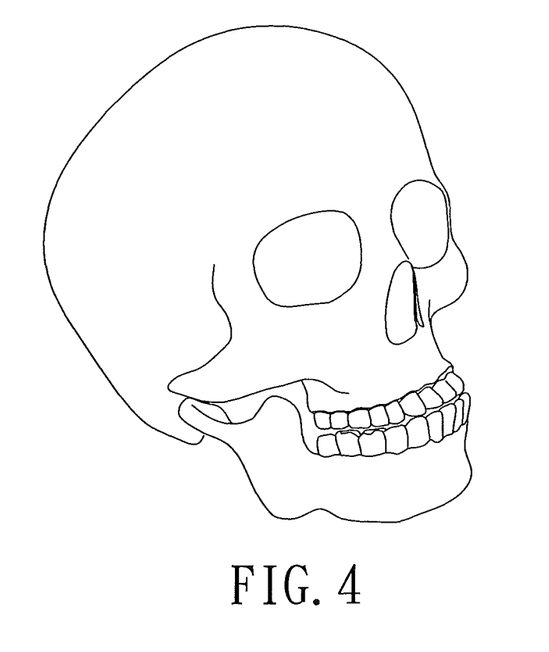
FIG. 4 shows a reconstructed 3D craniofacial image obtained from an image reconstruction step of the bone plate manufacturing method of the invention.

Referring to FIGS. 3 and 4, the image reconstruction step S2 uses the above image processing methods to perform image reconstruction for the original 3D craniofacial image, to obtain a reconstructed 3D craniofacial image. Note the image processing system contains the plurality of mechanical data of various parts of a human cranioface. More specifically, since the original 3D craniofacial image in FIG. 3 shows the condition of an affected part (injured part 1) of the cranioface (such as a compound fracture, a facial malformation and so on), the above image processing system is therefore required to perform the image reconstruction for the original 3D craniofacial image to obtain the reconstructed 3D craniofacial image. As an example, the patient may suffer from craniofacial complex fracture due to an external force, resulting in a crack (injured part 1) on the submaxillary of the patient that causes a malposition of the submaxillary as shown in FIG. 3. Thus, the image processing system is required to perform the image reconstruction and image editing for the injured cranioface of the patient. In the embodiment, the invention determines the range of image to be edited based on an image contrast and dynamic range and threshold, thereby obtaining the reconstructed 3D craniofacial image of the patient. Alternatively, the invention may obtain the reconstructed 3D craniofacial image of the patient by way of a mirror image acquisition that produces the reconstructed 3D craniofacial image based on the symmetry of the mirror image. As such, the uninjured craniofacial image of the patient can be obtained, as shown in FIG. 4. The spatial data of the original 3D craniofacial image and the reconstructed 3D craniofacial image are preferably stored in the database of the image processing system.

Figure 5:
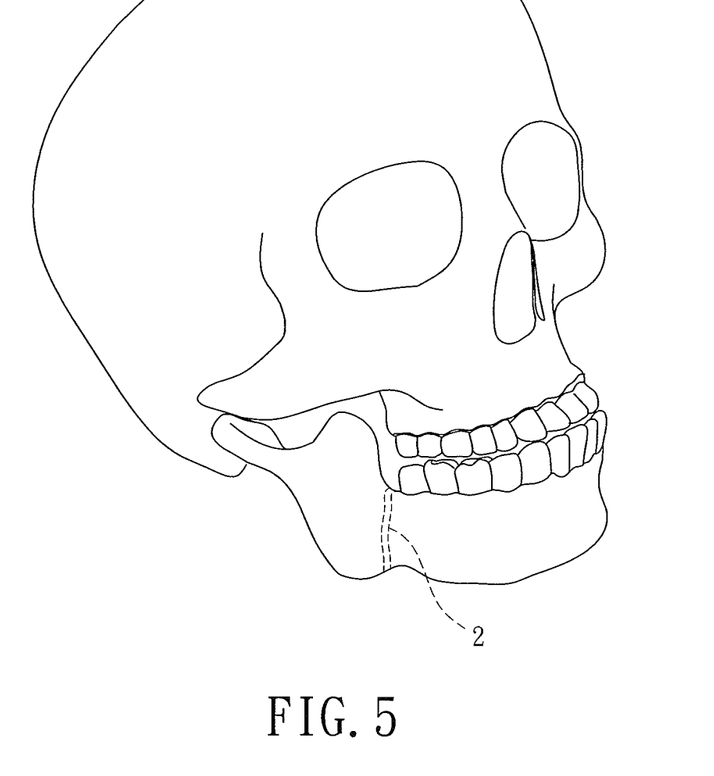
FIG. 5 shows a compared image obtained from a comparison step of the bone plate manufacturing method of the invention.

Referring to FIG. 5, the comparison step S3 is provided to compare the original 3D craniofacial image with the reconstructed 3D craniofacial image via the image processing system, and the image difference therebetween is defined as a defected portion 2. Specifically, the invention uses the image processing system to compare the spatial data between the original 3D craniofacial image and the reconstructed 3D craniofacial image to determine the defected portion 2. Since there must be some difference in spatial data between the original 3D craniofacial image and the reconstructed 3D craniofacial image (because the original 3D craniofacial image has the injured part 1 but the reconstructed 3D craniofacial image does not), the difference in spatial data may be defined as the defected portion 2.

Figure 6:
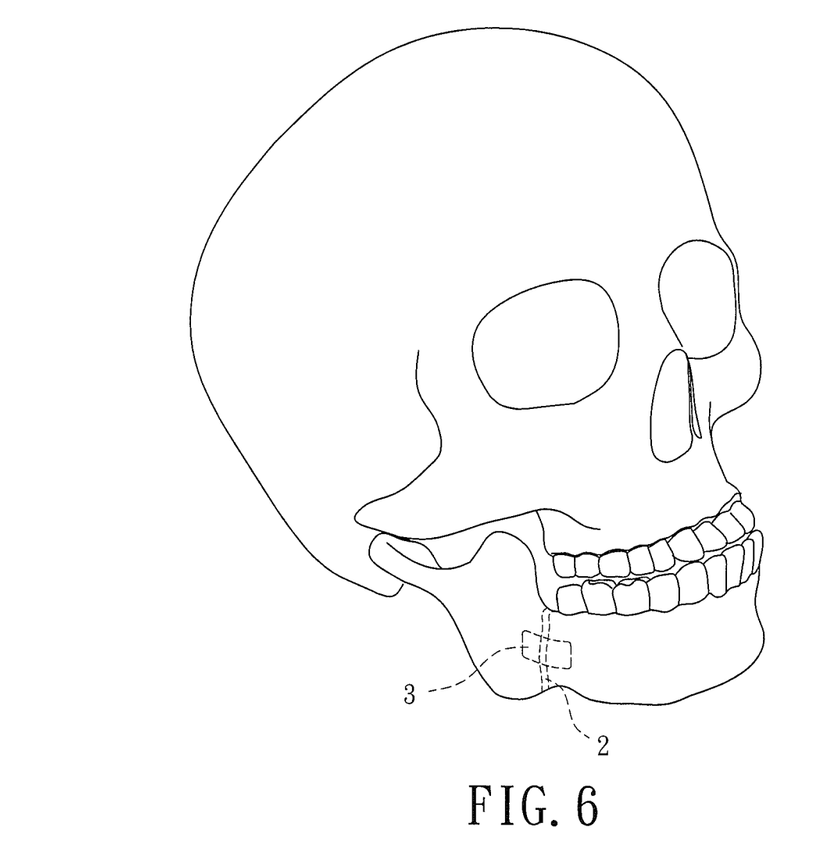
FIG. 6 shows the compared image with a mechanical compensation area according to the preferred embodiment of the invention.

Referring to FIG. 6, the data retrieval step S4 is provided to retrieve the mechanical data from the image processing system corresponding to the defected portion 2, and to define a mechanical compensation area 3 that compensates the mechanical data of the defected portion 2. Specifically, as shown in FIG. 6, the defected portion 2 is located on the submaxillary so that the mechanical data of the area of the submaxillary corresponding to the defected portion 2 is retrieved from the database of the image processing system. Then, the mechanical compensation area 3 may be defined on the reconstructed 3D craniofacial image based on the retrieved mechanical data, as shown in FIG. 6. The mechanical compensation area 3 is the location where a later-manufactured bone plate is placed. As such, the bone plate can compensate the force the defected portion 2 bears when the bone plate is placed on the mechanical compensation area 3. For example, the mechanical compensation area 3 is shown to cross the defected portion 2 to connect the craniofacial bones around the defected portion 2 together. This can compensate the longitudinal acting force of the submaxillary during an occlusion process thereof. Based on this, the force-bearing capability of the injured part 1 can be taken into consideration to produce a bone plate that better bears the stresses of the defected portion 2. Thus, the defected portion 2 will have better stability.

Figure 7:
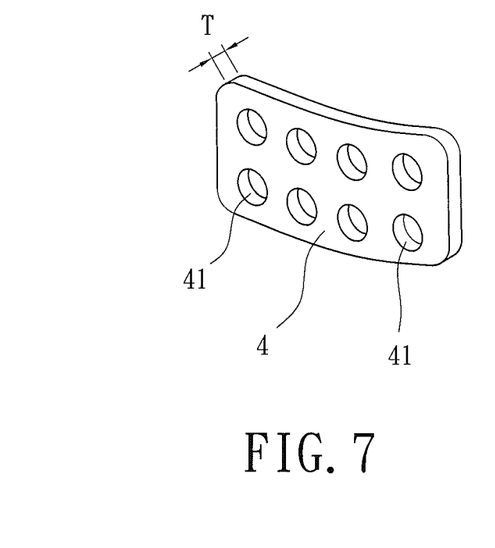
FIG. 7 shows a bone plate mold manufactured by a model designing step of the bone plate manufacturing method of the invention.

Referring to FIG. 7, the model designing step S5 is provided to design a bone plate mold 4 with a thickness T based on the surface shape of the mechanical compensation area 3, as shown in FIG. 7. This allows a face of the bone plate mold 4 to completely fit to the shape of the mechanical compensation area 3. Thus, the manufactured bone plate can be fully fitted to the mechanical compensation area 3 to improve the overall positioning efficiency and stability of the bone plate. This also provides the required support force and bearing force of the injured part 1. The bone plate mold 4 preferably comprises a plurality of positioning holes 41 according to the force-bearing capacity of the defected portion 2. The locations of the positioning holes 41 are determined based on the force-bearing capacity and force exertion direction of the defected portion 2 when the defected portion 2 is experiencing a usual craniofacial action. After the positioning holes 41 are determined, the bone plate manufactured by the bone plate mold 4 may be fixed on the mechanical compensation area 3 by fixing members (such as screws) extending through the positioning holes 41.

The data retrieval step S4 is provided to manufacture a bone plate using the bone plate mold 4. Specifically, the invention utilizes a processing unit to design the outline of the bone plate according to the bone plate mold 4 and manufactures the bone plate via machinery. The processing unit may be a CAD (computer-aided design), a CAM (computer-aided manufacturing) or a general processing system that implements computer designing. In this embodiment, the invention uses Boolean operations to determine the correspondence between the bone plate mold 4 and the compared image, designs the outline of the bone plate using a CAD according to the bone plate mold 4, and realizes the manufacture of the bone plate using the CAM. In the embodiment, the invention uses titanium metal to manufacture the bone plate.

The description of the bone plate manufacturing method of the invention is finished.

Figure 8:
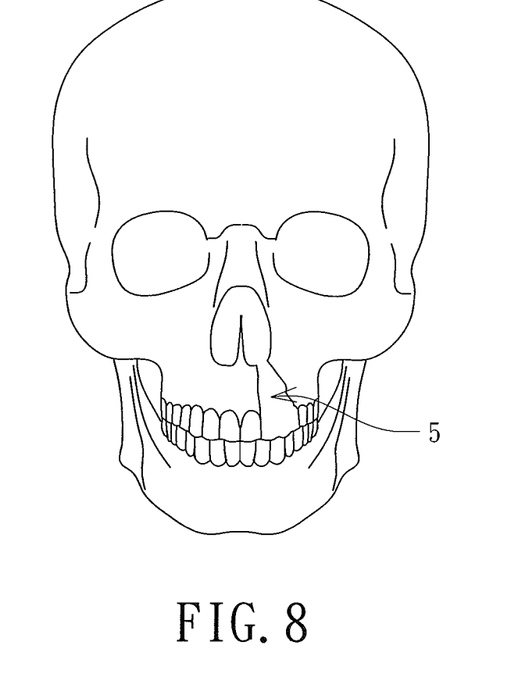
FIG. 8 shows a craniofacial malformation of a patient.

Referring to FIGS. 8 and 9, the patient may have a defected portion 5 on the lip and palate thereof resulting from tumor or congenital oral and maxillofacial malformation. The image processing system is preferably used to reconstruct the defected portion 5 of the cranioface of the patient so that a bone patch fitted to the defected portion 5 can be manufactured. Based on this, the bone plate manufacturing method can be used to manufacture a bone plate that fixes the bone patch to the cranioface of the patient. Thus, the bone plate manufacturing method can also benefit the patient with craniofacial defects.

Based on the description above, the bone plate manufacturing method of the invention defines the injured part by comparing the original 3D craniofacial image with the reconstructed 3D craniofacial image, and designs a tailor-made bone plate mold that takes the mechanical factor and spatiality of the injured part into consideration. Finally, the bone plate manufacturing method uses the CAD/CAM to design and manufacture the bone plate.

The bone plate manufacturing method of the invention is able to manufacture a tailor-made bone plate that has a general human craniofacial shape and can fit to the cranioface of any specific patient. In addition, the bone plate is positioned on an injured part of the cranioface of the patient based on the mechanical condition of the injured part. As an advantage, the manufactured bone plate can accurately fit to the cranioface of the patient that has an irregular structure, maintaining the functional integrity of the cranioface of the patient and increasing the probability of surgical success in craniofacial reconstruction.

Furthermore, the bone plate manufacturing method of the invention uses the image processing system and the processing unit to design the bone plate without always relying on the personal experiences of the surgeons, avoiding potential problems brought up by bone plate implantation such as damage in craniofacial functions or changes in looks. Thus, the bone plate manufacturing method can improve the accuracy of the craniofacial surgeries.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A bone plate manufacturing method, comprising:
   acquiring an original 3D craniofacial image of a patient;
   using an image processing system to perform an image reconstruction of the original 3D craniofacial image to obtain a reconstructed 3D craniofacial image, wherein the image processing system comprises a plurality of mechanical data specifying mechanical parameters of various parts of a cranioface;
   comparing the original 3D craniofacial image with the reconstructed 3D craniofacial image via the image processing system, and defining an image difference therebetween as a defected portion;
   retrieving a portion of the plurality of mechanical data that corresponds to the defected portion, and defining a mechanical compensation area on the reconstructed 3D craniofacial image that compensates the portion of the plurality of mechanical data of the defected portion;
   designing a bone plate mold with a thickness based on a surface shape of the mechanical compensation area; and
   manufacturing a bone plate using the bone plate mold.

2. The bone plate manufacturing method as claimed in claim 1, further comprising disposing a plurality of positioning holes on the bone plate mold.

3. The bone plate manufacturing method as claimed in claim 1, wherein manufacturing the bone plate comprises manufacturing the bone plate using a processing unit.

4. The bone plate manufacturing method as claimed in claim 3, wherein the processing unit is a Computer-Aided Design or a Computer-Aided Manufacturing.

5. The bone plate manufacturing method as claimed in claim 1, wherein the patient suffers from a craniofacial malformation due to a congenital or acquired injury.

6. The bone plate manufacturing method as claimed in claim 1, wherein the original 3D craniofacial image is obtained from a Computerized Axial Tomography or a Magnetic Resonance Imaging.

\* \* \* \* \*